United States Patent
Yune et al.

(10) Patent No.: US 10,772,866 B2
(45) Date of Patent: Sep. 15, 2020

(54) PHARMACEUTICAL COMPOSITION FOR PREVENTING AND TREATING CENTRAL NERVOUS SYSTEM DISEASES CONTAINING FLUOXETINE AND VITAMIN C AS ACTIVE INGREDIENTS

(71) Applicant: UNIVERSITY-INDUSTRY COOPERATION GROUP OF KYUNG HEE UNIVERSITY, Gyeonggi-do (KR)

(72) Inventors: Tae Young Yune, Seoul (KR); Hyung-Hwan Baik, Seoul (KR); Jee Youn Lee, Seoul (KR); Sam Kim, Seoul (KR)

(73) Assignee: UNIVERSITY-INDUSTRY COOPERATION GROUP OF KYUNG HEE UNIVERSITY, Gyeonggi-do (KR)

( * ) Notice: Subject to any disclaimer, the term of this patent is extended or adjusted under 35 U.S.C. 154(b) by 190 days.

(21) Appl. No.: 15/141,652

(22) Filed: Apr. 28, 2016

(65) Prior Publication Data
US 2016/0317492 A1 Nov. 3, 2016

Related U.S. Application Data

(63) Continuation of application No. PCT/KR2013/012427, filed on Dec. 31, 2013.

(30) Foreign Application Priority Data

Oct. 31, 2013 (KR) .................. 10-2013-0131730

(51) Int. Cl.
| | |
|---|---|
| *A61K 31/375* | (2006.01) |
| *A61K 31/138* | (2006.01) |
| *A23L 33/10* | (2016.01) |
| *A23L 33/15* | (2016.01) |
| *A61K 9/00* | (2006.01) |

(52) U.S. Cl.
CPC ............ *A61K 31/375* (2013.01); *A23L 33/10* (2016.08); *A23L 33/15* (2016.08); *A61K 9/0053* (2013.01); *A61K 31/138* (2013.01); *A23V 2002/00* (2013.01)

(58) Field of Classification Search
CPC ............................ A61K 31/375; A61K 31/138
See application file for complete search history.

(56) References Cited

U.S. PATENT DOCUMENTS

| | | | |
|---|---|---|---|
| 9,254,281 B2 * | 2/2016 | Corbett | ............. A61K 31/366 |
| 2013/0065924 A1 | 3/2013 | Corbett | |

FOREIGN PATENT DOCUMENTS

KR     101129303 B1     3/2012

OTHER PUBLICATIONS

Lee et al. Fluoxetine inhibits matrix metalloprotease activation and prevents disruption of blood-spinal cord barrier after spinal cord injury. Brain, (Aug. 2012) vol. 135, No. Part 8, pp. 2375-2389. abstract.*
Katoh et al. Effect of dietary vitamin C on compression injury of the spinal cord in a rat mutant unable to synthesize ascorbic acid and its correlation with that of vitamin E. Spinal Cord, (1996) vol. 34, No. 4, pp. 234-238 abstract.*
Lee et al. "Fluoxetine and vitamin C synergistically inhibits blood-spinal cord barrier disruption and improves functional recovery after spinal cord injury" Neuropharmacology 109:78-87 (2016).
Lin et al. "Ascorbic acid prevents blood-brain barrier disruption and sensory deficit caused by sustained compression of primary somatosensory cortex," *Journal of Cerebral Blood Flow & Metabolism*, 30:1121-1136 (2010).
Lee et al. "Fluoxetine inhibits matrix metalloprotease activation and prevents disruption of blood-spinal cord barrier after spinal cord injury," *Brain*, 135:2375-2389 (2012).
Amr et al. "Efficacy of Vitamin C as an adjunct to fluoxetine therapy in pediatric major depressive disorder: a randomized, double-blind, placebo-controlled pilot study" *Nutrition Journal*, 12:31 http://www.nutritionj.com/content/12/1/31 (2013).

* cited by examiner

*Primary Examiner* — Jennifer M Kim
(74) *Attorney, Agent, or Firm* — Klarquist Sparkman, LLP

(57) ABSTRACT

The present invention relates to a pharmaceutical composition for the prevention and treatment of blood-brain barrier disorder and central nervous system diseases containing fluoxetine and vitamin C as active ingredients. Specifically, when low concentration of fluoxetine and vitamin C, which did not show any improved effect on the blood-brain barrier disorder and disruption of blood-spinal cord barrier when administered alone, were mixed and co-administered to an animal model with spinal cord injury and transient global ischemia, the co-administration significantly increased the effect of inhibiting the increase of permeability of blood-spinal cord barrier and the effect of inhibiting MMP-9 activation and the effect of alleviating the influx of blood cells in an animal model with spinal cord injury; and the effect of inhibiting the disruption of blood-brain barrier and the effect of recovering memory in a transient global ischemia animal model, compared to the single administration of fluoxetine or vitamin C at the same concentration. The results indicate the synergy effect and the decrease of side effects by the co-administration of the compound at a low concentration, and thus fluoxetine and vitamin C of the present invention can be effectively used as active ingredients for a pharmaceutical composition for the prevention and treatment blood-brain barrier disorder and central nervous system diseases.

4 Claims, 8 Drawing Sheets

[Figure 1]

S: Normal Group,
Veh: Negative Control Group,
Vit: Group administered with Vit C alone,
Flu: Group administered with Fluoxetine alone,
V+F: Group co-administered with Vit C and Fluoxetine.

[Figure 2]

S: Normal Group,
Veh: Negative Control Group,
Vit: Group administered with Vit C alone,
Flu: Group administered with Fluoxetine alone,
V+F: Group co-administered with Vit C and Fluoxetine.

[Figure 3]

S: Normal Group,
Veh: Negative Control Group,
Vit: Group administered with Vit C alone,
Flu: Group administered with Fluoxetine alone,
V+F: Group co-administered with Vit C and Fluoxetine.

[Figure 4]

Veh: Negative Control Group,

Vitamin C+Fluoxetin: Group co-administered with Vit C and Fluoxetine.

[Figure 5]

S: Normal Group,
Veh: Negative Control Group,
Vit: Group administered with Vit C alone,
Flu: Group administered with Fluoxetine alone,
V+F: Group co-administered with Vit C and Fluoxetine.

[Figure 6]

Sham: Normal Group,
Veh: Negative Control Group,
Vit: Group administered with Vit C alone,
Flu: Group administered with Fluoxetine alone,
V+F: Group co-administered with Vit C and Fluoxetine.

[Figure 7]
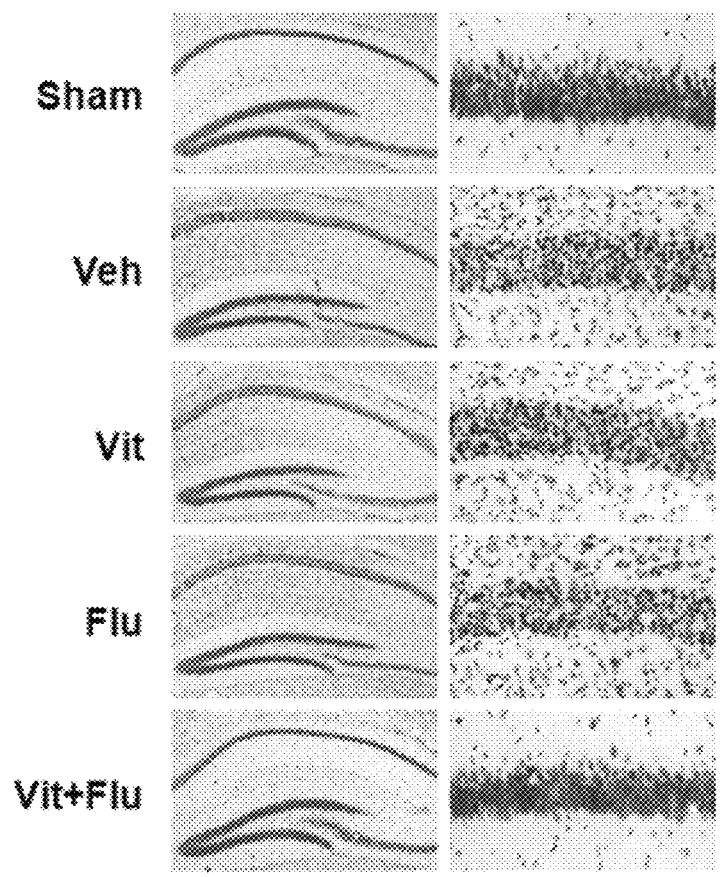
Sham: Normal Group,
Veh: Negative Control Group,
Vit: Group administered with Vit C alone,
Flu: Group administered with Fluoxetine alone,
Vit+Flu: Group co-administered with Vit C and Fluoxetine.

[Figure 8]
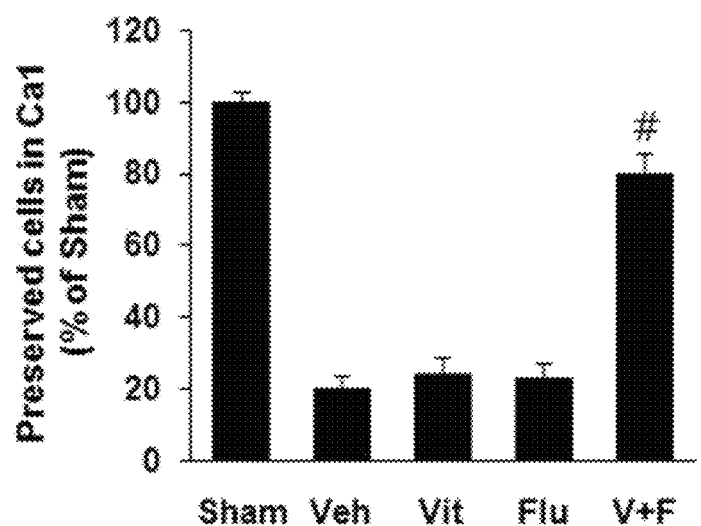
Sham: Normal Group,
Veh: Negative Control Group,
Vit: Group administered with Vit C alone,
Flu: Group administered with Fluoxetine alone,
V+F: Group co-administered with Vit C and Fluoxetine.

PHARMACEUTICAL COMPOSITION FOR PREVENTING AND TREATING CENTRAL NERVOUS SYSTEM DISEASES CONTAINING FLUOXETINE AND VITAMIN C AS ACTIVE INGREDIENTS

TECHNICAL FIELD

The present disclosure relates to a pharmaceutical composition for the prevention and treatment of blood-brain barrier disorders and central nervous system diseases containing fluoxetine and vitamin C as active ingredients.

BACKGROUND ART

There is a kind of a barrier present in the neural tissue that prevents particular materials from entering the blood vessels. This functional barrier is called blood-brain barrier (BBB, or blood-brain portal). Blood-brain barrier brain capillaries are capable of maintaining homeostasis of the microenvironment of neurons and are highly differentiated. The blood-brain barrier is a structure formed to maintain the transport of unnecessary materials at the minimum level due to a lower blood vessel permeability being maintained by the capillaries present in the neural tissue, compared to other tissues. The main structure establishing the blood-brain barrier consists of tight junctions or zonula occluden in the capillary endothelial cells. The fenestra, which is frequently seen in the capillaries of various other regions, is not present in the cytoplasm of the endothelial cells, and a pinocytotic vesicle is also present very rarely. Low molecular weight materials which are necessary for the neural tissue bind to carriers present in the cytoplasm and enter the brain parenchyma. Since the blood-brain barrier blocks the unspecific entry of ions, proteins, and other materials into the environment of central nervous system, the role as such a barrier enables the protection of neurons from harmful components being supplied from the blood while allowing essential materials to permeate therethrough. Most brain injuries such as cerebral infarction and trauma are associated with the disruption of the blood-brain barrier, and this in turn causes a secondary injury of neurons. Accordingly, the studies on the mechanism of generation and control of the blood-brain barrier are very important for the understanding and treatment of central nervous system diseases. Additionally, many kinds of drugs and metabolites cannot penetrate the blood-brain barrier, and thus an appropriate control of the blood-brain barrier can be very important for the administration of the drugs into the desired place in the treatment of various brain diseases including dementia.

In general, the blood-brain barrier may be considered as an organ to serve the role of protecting brain homeostasis. A blood-brain barrier disorder is associated with brain disorders. For example, vascular cerebral edema is the most common form of cerebral edema and it occurs due to the increase of permeability of capillaries. As the blood-brain barrier becomes loose due to a certain reason, the permeability to the blood serum proteins increases and the blood plasma filtrate leaks out through the intercellular space thereby causing cerebral edema. This is the major cause of dysfunction and death with symptoms such as seizure, brain infection, head injury, brain tumor, and multiple sclerosis. Additionally, multiple sclerosis causes activated autoreactive T cells to penetrate the blood-brain barrier. In the CNS, the above T cells induce a targeted inflammation response with respect to the myelin sheath and induce the disruption of the blood-brain barrier, autoantibodies and complement factors are introduced into the disrupted blood-brain barrier, thereby causing a demyelination process. Additionally, when the balance is broken in the neurotransmitters and minute ions in the extracellular fluid, it damages neuronal signaling, and subsequently the damage in the functionalization of recognition, neuropsychiatric impairment, or epileptic seizure. Additionally, impaired removal of damaged toxic proteins over the entire blood-brain barrier into the bloodstream has recently been proposed as a cause of neurodegenerative disorders such as Alzheimer's disease and prion diseases such as Creutzfeldt-Jakob disease and BSE. Accordingly, treatment of the functional disorder of the blood-brain barrier is suggested as a new solution to the treatment of brain disorders.

Fluoxetine is an antidepressant of the selective serotonin reuptake inhibitor (SSRI) class, and is used to treat depression, obsessive compulsive disorders, bulimia nervosa, anorexia nervosa, and panic disorders. Regarding the effects of fluoxetine other than as an antidepressant, it was reported to increase the anticonvulsive effect of carbamazepine, phenytoin, and ameltolide in the maximum electroconvulsive shock test using mice (Leander, J. D., 1992, *Epilepsai* 33: 573-576), and increase the effect of an antiepileptic agent co-administered with fluoxetine, and thus it was reported that fluoxetine can be useful for the treatment of depression patients with epilepsy. Recently, fluoxetine was reported to have an anti-inflammatory effect after ischemic injury and thus can be used for the protection effect of neurons (Lim, C. M. et. al, 2009, *J. Neurosci. Res.* 87, 1037-1045), and fluoxetine was also reported to inhibit the activity of matrix metalloproteinase (MMP) after spinal cord injury thereby being capable of preventing the disruption of blood spinal cord barrier (Lee, J. Y. et al, 2012, *Brain* 135, 2375-2389).

Vitamin C is one of trace elements necessary for the maintenance of functions and health of the human bodies and is also called ascorbic acid. Vitamin C helps human bodies to resist infections, heals injuries, helps to maintain tissues, and as one of antioxidants, is known to prevent cell damage by free radicals. Regarding the treatment of disruption of the blood-brain barrier and sensory defect, it was previously reported that vitamin C has the effect of alleviating the injuries in blood-brain barrier and sensory neurons induced by continuous compression (J-L Lin et al, 2010, *jcbfm* 30, 1121-1136). However, there has been no report regarding the effect of fluoxetine and vitamin C on the alleviation of the injury of blood-brain barrier.

SUMMARY

The present inventors have endeavored to develop a method for the effective treatment of blood-brain barrier disorders and central nervous system diseases while administering a composition at a low concentration, and as a result, they have confirmed that when a low concentration of fluoxetine and vitamin C, which did not show any improved effect on the blood-brain barrier disorders and disruption of blood-spinal cord barrier when administered alone, were mixed and co-administered to an animal model with spinal cord injury and transient global ischemia, the co-administration significantly increased the effect of inhibiting the increase of permeability of blood-spinal cord barrier and the effect of inhibiting MMP-9 activation and the effect of alleviating the influx of blood cells in an animal model with spinal cord injury; and the effect of inhibiting the disruption of blood-brain barrier and the effect of recovering memory in a transient global ischemia animal model, and these effects were significantly higher, compared to the single administration of fluoxetine or vitamin C at the same concentration, thereby completing the present invention.

Technical Problem

One object of the present invention is to provide a pharmaceutical composition for the prevention and treatment of blood-brain barrier (BBB) disorders and central nervous system diseases containing low concentrations of fluoxetine and vitamin C.

Technical Solution

In order to achieve the objects, the present invention provides a pharmaceutical composition for the prevention and treatment of a blood-brain barrier (BBB) disorders containing fluoxetine and vitamin C as active ingredients.

Additionally, the present invention provides a pharmaceutical composition for the prevention and treatment of central nervous system diseases containing fluoxetine and vitamin C as active ingredients.

Additionally, the present invention provides a health food for preventing and alleviating blood-brain barrier disorders containing fluoxetine and vitamin C as active ingredients.

Additionally, the present invention provides a health food for preventing and alleviating central nervous system diseases containing fluoxetine and vitamin C as active ingredients.

Additionally, the present invention provides a method for the treatment of blood-brain barrier disorders, including administering fluoxetine and vitamin C to a subject having blood-brain barrier disorders.

Additionally, the present invention provides a method for the treatment of central nervous system diseases, including administering fluoxetine and vitamin C to a subject having blood-brain barrier disorders.

Additionally, the present invention provides a method for the prevention of blood-brain barrier disorders, including administering an effective amount of fluoxetine and vitamin C to a subject.

Additionally, the present invention provides a method for the prevention of central nervous system diseases, including administering an effective amount of fluoxetine and vitamin C to a subject.

Additionally, the present invention provides fluoxetine and vitamin C for use as a pharmaceutical composition for the prevention and treatment of blood-brain barrier disorders.

Additionally, the present invention provides fluoxetine and vitamin C for use as a pharmaceutical composition for the prevention and treatment of central nervous system diseases.

Additionally, the present invention provides fluoxetine and vitamin C for use as a health food for the prevention and treatment of blood-brain barrier disorders.

Additionally, the present invention provides fluoxetine and vitamin C for use as a health food for the prevention and treatment of central nervous system diseases.

Advantageous Effects

Since fluoxetine and vitamin C of the present invention were mixed at a trace amount, at which no significant effect on the alleviation of blood-brain barrier disorders was known, the combination showed a synergistic effect on the disruption of blood-brain barrier disorders and a decrease of side effects due to the administration of the compound at a low concentration in animal models with spinal cord injury and transient global ischemia, compared to the single administration of fluoxetine and vitamin C, respectively. Therefore, the composition containing fluoxetine and vitamin C of the present invention can be effectively used as active ingredients for a pharmaceutical composition for the prevention and treatment blood-brain barrier disorders.

BRIEF DESCRIPTION OF THE DRAWINGS

FIG. 1 shows the effect of the co-treatment of fluoxetine and vitamin C on inhibiting the increase of the permeability of blood-spinal cord barrier regarding the blood-spinal cord barrier (BSCB) injury after spinal cord injury, in which:

FIG. 2 shows the effect of the co-treatment of fluoxetine and vitamin C on inhibiting the activity of matrix metalloproteinase-9 (MMP-9) after spinal cord injury, in which:

FIG. 3 shows the expression of a macrophage marker according to the co-treatment of fluoxetine and vitamin C after spinal cord injury, in which:

FIG. 4 shows the effect of alleviating infiltration of inflammatory cells according to the co-treatment of fluoxetine and vitamin C after spinal cord injury, in which:

FIG. 5 shows the effect of the co-treatment of fluoxetine and vitamin C on inhibiting the disruption of blood-brain barrier (BBB) after transient global ischemia, in which:

FIG. 6 shows the effect of the co-treatment of fluoxetine and vitamin C on memory recovery regarding the hippocampal-dependent short-term memory after transient global ischemia, in which:

FIG. 7 shows the hippocampal tissues of animal models with transient global ischemia.

FIG. 8 shows the percentage of neuronal cells remaining in the hippocampal neuron area (preserved cells) in animal models with transient global ischemia (# indicates the result of significant difference compared to that of negative control group (vehicle)).

MODE FOR CARRYING OUT THE INVENTION

Figure 1A:
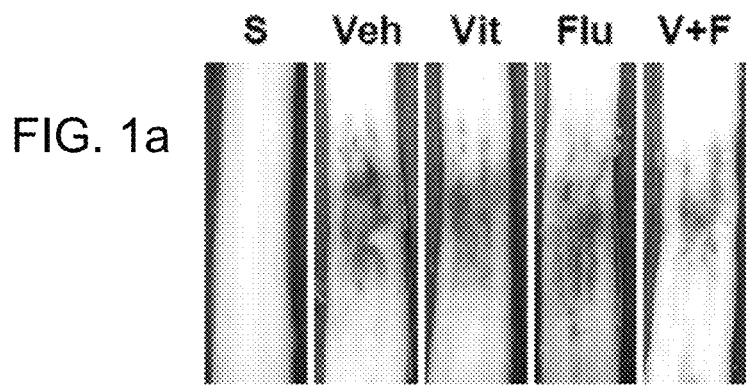
FIG. 1A shows the spinal cord of an animal model with spinal cord injury, in which Evans Blue was deposited.

Hereinafter, the present invention will be explained in detail.

The present invention provides a pharmaceutical composition for the prevention and treatment of blood-brain barrier disorders containing fluoxetine and vitamin C as active ingredients.

Fluoxetine and vitamin C are preferably mixed in a ratio from 1:500 to 1:10, specifically, more preferably mixed in a ratio from 1:200 to 1:50, and more specifically, most preferably mixed in a ratio from 1:100, but the mixing ratio is not limited thereto.

Fluoxetine is preferably included at a concentration of 0.1 mg/kg to 10 mg/kg, specifically, more preferably included 0.5 mg/kg to 5 mg/kg, more specifically, most preferably included 0.8 mg/kg to 2 mg/kg, but the content is not limited thereto. When fluoxetine is included more than 10 mg/kg, fluoxetine alone can exhibit the effects of prevention and treatment of the blood-brain barrier disorders, whereas when fluoxetine is included equal to or less than 10 mg/kg, fluoxetine alone cannot exhibit the effects of prevention and treatment of the blood-brain barrier disorders. However, in the co-administration of fluoxetine and vitamin C of the present invention, fluoxetine at a concentration of equal to or less than 10 mg/kg exhibits a synergy effect against blood-brain barrier disorders and the effect of reduced side effects and is thus effective.

Vitamin C is preferably included at a concentration of 10 mg/kg to 500 mg/kg, specifically, more preferably included 50 mg/kg to 200 mg/kg, more specifically, most preferably included 70 mg/kg to 150 mg/kg, but the content is not limited thereto.

When vitamin C is included more than 500 mg/kg, vitamin C alone can exhibit the effects of prevention and treatment of the blood-brain barrier disorders (Jia-Li Lin et. al, Journal of cerebral blood flow & metabolism (2010) 30, 1121-1136), whereas when vitamin C is included equal to or less than 500 mg/kg, vitamin C alone cannot exhibit the effects of prevention and treatment of the blood-brain barrier disorders. However, in the co-administration of fluoxetine and vitamin C of the present invention, vitamin C at a concentration of equal to or less than 500 mg/kg exhibits a synergy effect against blood-brain barrier disorders and the effect of reduced side effects and is thus effective.

The blood-brain barrier disorder is preferably one selected from the group consisting of spinal cord injury, chronic or acute stroke, cerebral infarction, brain tumor, cerebral edema, brain ischemia, Alzheimer's disease, and multiple sclerosis, but is not limited thereto.

In an exemplary embodiment of the present invention, the present inventors prepared an animal model with spinal cord injury by co-administration of fluoxetine (1 mg/kg) and vitamin C (100 mg/kg) after inducing spinal cord injury in rats. Additionally, as a result of confirming the inhibitory effect against the increase of permeability regarding the blood-spinal cord barrier (BSCB) injury after spinal cord injury, it was confirmed that when the co-administration of fluoxetine and vitamin C inhibited the increase of permeability to a level of about 50%, compared to the negative control group and the groups administered with vitamin C or fluoxetine alone, thereby exhibiting a significant therapeutic effect of about a 2-fold against the blood-spinal cord barrier damage after spinal cord injury (see FIG. 1).

Additionally, the present inventors have confirmed the enzyme activity of MMP-9, which is known to be involved in the disruption of blood-spinal cord barrier and inflammatory response in the animal model with the spinal cord injury, and as a result, they have confirmed that the co-administration of fluoxetine and vitamin C inhibit the enzyme activity of MMP-9 to a level of about 50%, compared to the negative control group, the group administered with vitamin C alone, and the group administered with fluoxetine alone, thereby exhibiting a significant therapeutic effect of about a 2-fold against the disruption of blood-spinal cord barrier and inflammatory response (see FIG. 2).

Figure 3A:
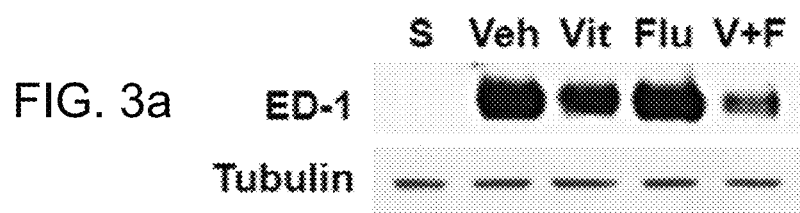
FIG. 3A shows the expression of ED-1 protein in an animal model with spinal cord injury.
Figure 3B:
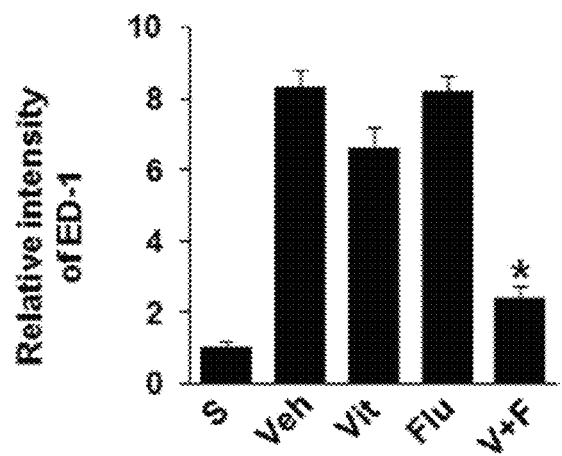
FIG. 3B shows the relative intensity of the activity of ED-1 protein (* indicates the result of significant difference compared to that of negative control group (vehicle)).
Figure 4A:
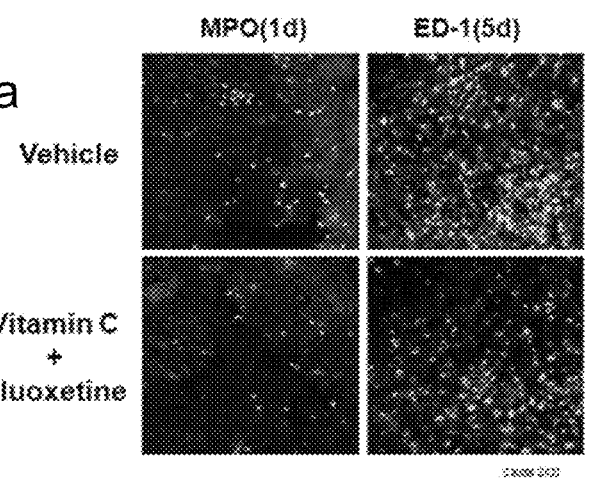
FIG. 4A shows the expression of myeloperoxidase (MPO), which is a neutrophil marker, one day after the administration of vitamin C and fluoxetine and the expression of ED-1 five days after the administration of vitamin C and fluoxetine in an animal model with spinal cord injury.
Figure 4C:
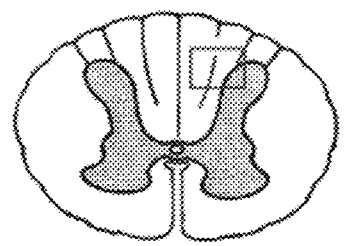
FIG. 4C shows the position of the spinal cord tissue in which the expression levels of MPO and ED-1 were measured.
Figure 4B:
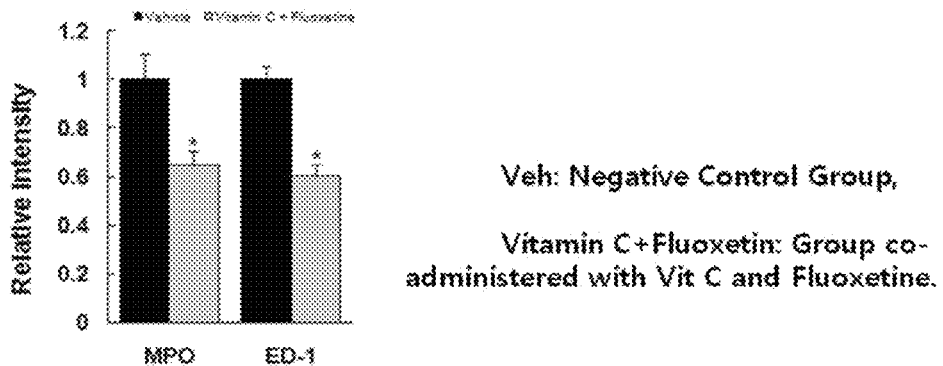
FIG. 4B shows the relative intensity regarding the intracellular expression of MPO and ED-1 in an animal model with spinal cord injury (* indicates the result of significant difference compared to that of negative control group (vehicle))

Additionally, for confirming the effect of alleviating the influx of blood cells in the animal model with spinal cord injury, the present inventors have also confirmed the expression of ED-1, which is a macrophage marker, and myeloperoxidase (MPO), which is a neutrophil marker, as a result, they have confirmed that the co-administration of fluoxetine and vitamin C inhibited the expression of ED-1 protein to about 25% level, compared to the negative control group, the group administered with vitamin C alone, and the group administered with fluoxetine alone, thereby exhibiting a significant effect (see FIG. 3), and also confirmed that the co-administration of fluoxetine and vitamin C inhibited the intracellular expression of the markers to about 60% level, compared to the negative control group (see FIG. 4).

Additionally, the present inventors prepared an animal model with transient global ischemia by inducing transient global ischemia in mice followed by co-administration with fluoxetine (1 mg/kg) and vitamin C (100 mg/kg). In order to confirm the inhibitory effect of the co-administration against the disruption of blood-brain barrier in the animal model, the mice were injected with Evans Blue dye and the amount of Evans Blue dye which penetrated into the damaged blood-brain barrier and flown into the fore brain was examined. As a result, they have confirmed that, in the group co-administered with fluoxetine and vitamin C, the increase of permeability was inhibited to about 50% of those of the negative control group, the group administered with vitamin C alone, and the group administered with fluoxetine, thus exhibiting a significant therapeutic effect of the co-administration by about a 2-fold regarding the blood-brain barrier damage due to transient global ischemia (see FIG. 5).

Additionally, the present inventors have confirmed the effect of hippocampal-dependent short-term memory in the animal model with transient global ischemia, and as a result, confirmed that the group co-administered with fluoxetine and vitamin C showed a significant increase of short-term memory compared to the negative control group, the group administered with vitamin C alone, and the group administered with fluoxetine (see FIG. 6), and also confirmed that the degree of cell damage in the CA1 neuron region of hippocampal tissue was decreased thereby showing a significant effect of recovering the neurons to a level similar to those of the normal group (see FIGS. 7 and 8).

Accordingly, the co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used as active ingredients of a pharmaceutical composition for the prevention and treatment of blood-brain barrier disorder.

The composition of the present invention may be prepared in various forms for oral or parenteral administration. For formulations, commonly used fillers, extenders, binders, humectants, disintegrating agents, diluents such as surfactants or excipients may be used.

Solid preparations for oral administration include tablets, pills, powders, granules, capsules, etc. The above solid preparations may be prepared by adding at least one excipient, e.g., starch, calcium carbonate, sucrose, lactose, gelatin, etc., to at least one compound. Additionally, lubricants such as magnesium stearate, talc, etc., may be used in addition to the simple excipients. Examples of liquid preparations for oral administration include suspensions, preparations for internal use, emulsifiers, syrups, etc., and various kinds of excipients, e.g., humectants, sweeteners, fragrants, preservatives, etc., may be used in addition to simple diluents such as water and liquid paraffin.

Formulations for parenteral administration may include sterile aqueous solutions, non-aqueous solvents, suspensions, emulsions, lyophilized formulations, suppositories, etc. Examples of the non-aqueous solvents and suspensions may include a vegetable oil such as propylene glycol, polyethylene glycol, and olive oil, an injectable ester such as ethyl oleate, etc. Examples of bases for suppositories may include Witepsol, macrogol, Tween 61, cacao butter, laurinum, glycerol, gelatin, etc.

The composition of the present invention may be prepared in orally or parenterally. For parenteral administration, it is preferable to the use for external skin or peritoneal-, rectal-, intravenous-, intramuscular-, subcutaneous-, intrauterine-, or intracerebrovascular injection, and most preferably the use external skin.

The composition of the present invention is administered in a pharmaceutically effective amount. As used herein, the term "pharmaceutically effective amount" refers to an amount sufficient for the treatment of diseases at a reasonable benefit/risk ratio applicable to a medical treatment, and the level of the effective dose may be determined based on the factors including the kind of a disease, severity of illness, drug activity, drug sensitivity, administration time, administration route and dissolution rate, length of treatment, factors including drug(s) to be concurrently used in combination, and other factors well known in the medical field. The composition of the present invention may be administered as an individual therapeutic agent, in combination with other therapeutic agents, or sequentially or simultaneously with a conventional therapeutic agent(s), and may be administered once or multiple times. It is important to administer an amount to obtain the maximum effect with a minimum amount without adverse effects, considering the factors described above, and these factors can easily be determined by one of ordinary skill in the art.

The dose of the composition of the present invention may vary widely depending on body weight, age, sex, health conditions, diet of a patient, administration time, administration route, excretion rate and severity of illness, and may be administered once to six times daily. However, the dose may be increased or decreased according to the administration route, severity of obesity, sex, body weight, age, etc., and thus the dose should not limit the scope of the present invention in any manner.

The composition of the present invention may be used alone or in combination with surgery, radiation therapy, hormone treatment, chemical treatment, and used of biological response controlling agents.

The present invention provides a pharmaceutical composition for the prevention and treatment of central nervous system diseases containing fluoxetine and vitamin C as active ingredients.

The Fluoxetine and vitamin C are preferably mixed in a ratio from 1:500 to 1:10, specifically, more preferably mixed in a ratio from 1:200 to 1:50, and more specifically, most preferably mixed in a ratio from 1:100, but the mixing ratio is not limited thereto.

Fluoxetine is preferably included at a concentration of 0.1 mg/kg to 10 mg/kg, specifically, more preferably included 0.5 mg/kg to 5 mg/kg, more specifically, most preferably included 0.8 mg/kg to 2 mg/kg, but the content is not limited thereto. When fluoxetine is included more than 10 mg/kg, fluoxetine alone can exhibit the effects of prevention and treatment of central nervous system diseases, whereas when fluoxetine is included equal to or less than 10 mg/kg, fluoxetine alone cannot exhibit the effects of prevention and treatment of central nervous system diseases. However, in the co-administration of fluoxetine and vitamin C of the present invention, fluoxetine at a concentration of equal to or less than 10 mg/kg exhibits a synergy effect against central nervous system diseases and the effect of reduced side effects and is thus effective.

Vitamin C is preferably included at a concentration of 10 mg/kg to 500 mg/kg, specifically, more preferably included 50 mg/kg to 200 mg/kg, more specifically, most preferably included 70 mg/kg to 150 mg/kg, but the content is not limited thereto.

When vitamin C is included more than 500 mg/kg, vitamin C alone can exhibit the effects of prevention and treatment of central nervous system diseases, whereas when vitamin C is included equal to or less than 500 mg/kg, vitamin C alone cannot exhibit the effects of prevention and treatment of central nervous system diseases. However, in the co-administration of fluoxetine and vitamin C of the present invention, vitamin C at a concentration of equal to or less than 500 mg/kg exhibits a synergy effect against central nervous system diseases and the effect of reduced side effects and is thus effective.

The central nervous system disease is preferably one selected from the group consisting of spinal cord injury, chronic or acute stroke, cerebral infarction, brain tumor, cerebral edema, brain ischemia, Alzheimer's disease, and multiple sclerosis, but is not limited thereto.

The co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used as active ingredients of a pharmaceutical composition for the prevention and treatment of blood-brain barrier disorder.

Additionally, the present invention provides a health food for preventing and alleviating blood-brain barrier disorder containing fluoxetine and vitamin C as active ingredients.

Additionally, the present invention provides a health food for preventing and alleviating central nervous system diseases containing fluoxetine and vitamin C as active ingredients.

Fluoxetine and vitamin C are preferably mixed in a ratio from 1:500 to 1:10, specifically, more preferably mixed in a ratio from 1:200 to 1:50, and more specifically, most preferably mixed in a ratio from 1:100, but the mixing ratio is not limited thereto.

Fluoxetine is preferably included at a concentration of 0.1 mg/kg to 10 mg/kg, specifically, more preferably included 0.5 mg/kg to 5 mg/kg, more specifically, most preferably included 0.8 mg/kg to 2 mg/kg, but the content is not limited thereto. When fluoxetine is included more than 10 mg/kg, fluoxetine alone can exhibit the effects of prevention and treatment of blood-brain barrier disorder or central nervous system diseases, whereas when fluoxetine is included equal to or less than 10 mg/kg, fluoxetine alone cannot exhibit the effects of prevention and treatment of blood-brain barrier disorder or central nervous system diseases. However, in the co-administration of fluoxetine and vitamin C of the present invention, fluoxetine at a concentration of equal to or less than 10 mg/kg exhibits a synergy effect against blood-brain barrier disorder or central nervous system diseases and the effect of reduced side effects and is thus effective.

Vitamin C is preferably included at a concentration of 10 mg/kg to 500 mg/kg, specifically, more preferably included 50 mg/kg to 200 mg/kg, more specifically, most preferably included 70 mg/kg to 150 mg/kg, but the content is not limited thereto.

When vitamin C is included more than 500 mg/kg, vitamin C alone can exhibit the effects of prevention and treatment of blood-brain barrier disorder or central nervous system diseases, whereas when vitamin C is included equal to or less than 500 mg/kg, vitamin C alone cannot exhibit the effects of prevention and treatment of blood-brain barrier disorder or central nervous system diseases. However, in the co-administration of fluoxetine and vitamin C of the present invention, vitamin C at a concentration of equal to or less than 500 mg/kg exhibits a synergy effect against blood-brain barrier disorder or central nervous system diseases and the effect of reduced side effects and is thus effective.

The blood-brain barrier disorder or central nervous system diseases is preferably one selected from the group consisting of spinal cord injury, chronic or acute stroke, cerebral infarction, brain tumor, cerebral edema, brain ischemia, Alzheimer's disease, and multiple sclerosis, but is not limited thereto.

The co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used as active ingredients of a health food for preventing and alleviating blood-brain barrier disorder and central nervous system diseases.

There is no particular limitation on the kinds of foods of the present invention. Examples of the foods in which the above materials can be added may include drinks, meats, sausages, bread, biscuits, rice cakes, chocolates, candies, snacks, cookies, pizzas, ramens, other noodles, gums, dairy products including ice cream, various kinds of soups, beverages, alcoholic beverages, vitamin complexes, milk products, milk processed products, etc., and may include all kinds of health functional foods from the conventional point of view.

The fluoxetine and vitamin C of the present invention may be directly added to foods as they are or may be used along with other foods or food components, and may be appropriately used according to the conventional method. The mixed amount of the active ingredients may be appropriately determined according to the purpose of their use (prevention or alleviation). In general, the amount of the above compounds in health foods may be included in an amount of from 0.1 parts by weight to 90 parts by weight relative to the total amount of the food. However, in the case of a long-term intake for the purpose of health and hygiene or health control, the amount to be included may be less than the above range, but since they have no safety problem they may be used more than the above range as active ingredients.

The health functional drink composition of the present invention is not particularly limited regarding other ingredients except for containing the fluoxetine and vitamin C in an indicated ratio as essential ingredients, and various kinds of flavoring agents or natural carbohydrates, etc., may be further included as additionally ingredients along with the conventional drinks. Examples of the natural carbohydrates may include the conventional sugars such as monosaccharides, e.g., glucose, fructose, etc.; disaccharides, e.g., maltose, sucrose, etc.; and polysaccharides, e.g., dextrin, cyclodextrin, etc.; and sugar alcohols such as xylitol, sorbitol, erythritol, etc. As flavoring agents other than those described above, natural flavoring agents (thaumatin, stevia extracts (e.g., rebaudiocide A, glycyrrhizin, etc.) and synthetic flavoring agents (saccharin, aspartame, etc.) may be advantageously used. The content of natural carbohydrates may be generally about 1 g to 20 g, and preferably about 5 g to 12 g, relative to 100 g of the composition of the present invention.

In addition to those described above, the health food of the present invention may contain various nutrients, vitamins, minerals (electrolytes), flavoring agents such as synthetic and natural flavoring agents, coloring agents and flavor enhancers (cheese, chocolates, etc.), pectic acid and a salt thereof, alginic acid and a salt thereof, organic acids, protective colloid thickeners, pH adjusters, stabilizers, preservatives, glycerin, alcohol, carbonating agents used in carbonated drinks, etc. In addition, the health food of the present invention may contain fruit flesh for the preparation of natural fruit juices and fruit juice drinks and vegetable drinks. These ingredients may be used independently or in combination. The content of these additives may not be critical but they are generally selected in the range of from about 0.1 parts by weight to about parts by weight relative to 100 parts by weight of the fluoxetine and vitamin C of the present invention.

Additionally, the present invention provides a method for treating blood-brain barrier disorder including administering fluoxetine and vitamin C to a subject having blood-brain barrier disorder.

Additionally, the present invention provides a method for treating blood-brain barrier disorder including administering fluoxetine and vitamin C to a subject having central nervous system diseases.

The co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used as a method for treating blood-brain barrier disorder and central nervous system diseases.

Additionally, the present invention provides a method for preventing blood-brain barrier disorder including administering an effective amount of fluoxetine and vitamin C to a subject.

Additionally, the present invention provides a method for preventing central nervous system diseases including administering an effective amount of fluoxetine and vitamin C to a subject.

The co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used as a method for preventing blood-brain barrier disorder and central nervous system diseases.

Additionally, the present invention provides fluoxetine and vitamin C to be used for a pharmaceutical composition for the prevention and treatment of blood-brain barrier disorder.

Additionally, the present invention provides fluoxetine and vitamin C to be used for a pharmaceutical composition for the prevention and treatment of central nervous system diseases.

The co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used as a method for preventing and treating blood-brain barrier disorder and central nervous system diseases.

Additionally, the present invention provides fluoxetine and vitamin C to be used for a health food for preventing and alleviating blood-brain barrier disorder.

Additionally, the present invention provides fluoxetine and vitamin C to be used for a health food for preventing and alleviating central nervous system diseases.

The co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used as a health food for preventing and treating blood-brain barrier disorder and central nervous system diseases.

Hereinafter, the present invention will be described in details with reference to Examples and Preparation Examples.

However, the following Examples and Preparation Examples are provided for illustrative purposes and the scope of the present invention should not be limited by the Examples and Preparation Examples.

EXAMPLE 1

Preparation of an Animal Model with Spinal Cord Injury

<1-1> Preparation of an Animal Model with Spinal Cord Injury

Adult male Sprague Dawley rats (Samtako Inc., Korea) were anesthetized by intraperitoneally administering with choral hydrate (500 mg/kg), and the $8^{th}$ to the parts of the $10^{th}$ thoracic vertebra were exposed. Then, a 10 g weight was dropped from a predetermined height onto the thoracic vertebra of the anesthetized rats to give an injury similar to that of human spinal cord injury, and an animal model with spinal cord injury was performed using the NYU impactor (Routes, Cytec Korea, Inc.) designed for digitization of injury intensity in a computer. After confirming that a certain injury was given within the predetermined error range based on the data regarding the injury intensity shown in the computer, the injured region was sutured, disinfected with Povidin liquid, and put into cages (2 rats/cage) and bred. The urination of the rats was assisted by performing artificially massaging their urinary bladders 3 times daily.

<1-2> Administration of Fluoxetine and Vitamin C

After inducing spinal cord injury in Example <1-1>, the rats were co-administered by intraperitoneal injection with fluoxetine and vitamin C, which were dissolved in physiological saline at concentrations of 1 mg/kg and 100 mg/kg, respectively, once daily for 5 days. Physiological saline not containing fluoxetine and vitamin C was used as the negative control while a single administration of fluoxetine and vitamin C, which were respectively dissolved in physiological saline at concentrations of 1 mg/kg or 100 mg/kg, were used as the comparative control groups.

<1-3> Preparation of Spinal Cord Tissue

The animal model prepared in Example <1-2> was subjected to perfusion via right atrium and fixed with 4% paraformaldehyde, and the spinal cord nerve was cut and embedded with an optimum cutting temperature (OCT) compound, and then cut off using a cryostat. The spinal cord tissue, which was cut for the isolation of RNA and proteins, was perfused using phosphate buffered saline (PBS), and cut into a size of 1 cm around the injured area, frozen in liquid nitrogen, and stored at −80° C. until use.

EXAMPLE 2

Confirmation of the Inhibitory Effect of the Co-Treatment of Fluoxetine and Vitamin C Against the Increase of Blood-Spinal Cord Barrier Permeability Regarding the Blood-Spinal Cord Barrier (BSCB) Injury after Spinal Cord Injury In order to confirm the effect of the co-treatment of fluoxetine and vitamin C, when they were co-treated, on the blood-spinal cord barrier injury after the spinal cord injury, the change in permeability according to the disruption of the blood-spinal cord barrier was confirmed using Evans Blue dye.

Specifically, the animal model with spinal cord injury prepared in the same manner as in Example <1-2> was intraperitoneally administered with 5 mL of 2% Evans Blue dye dissolved in physiological saline, perfused 3 hours thereafter with PBS, and confirmed the change in permeability of the blood-spinal cord barrier in the spinal cord with injury. Then, the spinal cord tissue was cut into a size of 4 mm centered on the injured area by performing in the same manner as in Example <1-3>, added with 50% trichloroacetic acid solution to grind the tissue, centrifuged at 10,000×g for 10 minutes to obtain the supernatant, and the fluorescence of the excitation wavelength at 620 nm and the emission wavelength at 680 nm was measured. An animal model not induced with spinal cord injury was used as the normal group, the negative control group was administered with physiological saline not containing fluoxetine and vitamin C, and the comparative control group was administered with fluoxetine or vitamin C alone after dissolving them in physiological saline at a concentration of 1 mg/kg or 100 mg/kg, respectively.

Figure 1B:
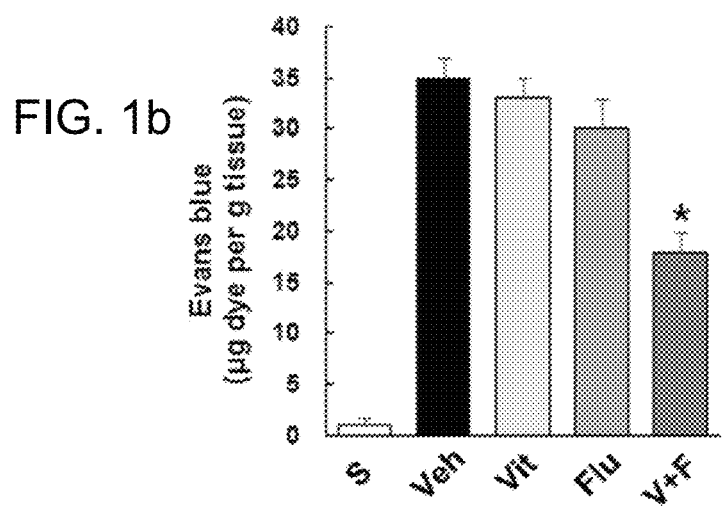
FIG. 1B shows the amount of Evans Blue dye quantitated in the spinal cord of an animal model with spinal cord injury (* indicates the result of significant difference compared to that of negative control group (vehicle)).

As a result, as shown in FIG. 1, it was confirmed that the co-treatment of vitamin C and fluoxetine at a trace amount significantly increased the inhibitory effect against the disruption of the blood-spinal cord barrier, whereas a single respective treatment of vitamin C or fluoxetine at a trace amount showed a degree of disruption of the blood-spinal cord barrier similar to that of the negative control group (FIGS. 1a and 1b).

EXAMPLE 3

Confirmation of the Effect of the Co-Treatment of Fluoxetine and Vitamin C Inhibiting the Activity Matrix Metalloproteinase-9 (MMP-9) after Spinal Cord Injury In order to confirm the effect of the co-treatment of fluoxetine and vitamin C, when they were co-treated, on the alleviation of spinal cord injury, the degree of activity of MMP-9, which is known to be involved in disruption of blood-spinal cord barrier and inflammation response, was confirmed via zymography.

Specifically, spinal cord tissue slices at a size of 10 μm were prepared in the same manner as in Example <1-2>, the spinal cord tissue slices were added with a lysis buffer containing octylphenoxy polyethoxy ethanol (Nonidet P-40, NP-40), 150 mM NaCl, 0.5% sodium deoxycholate, 0.1% SDS, and 50 mM tris (pH 8.0), and intracellular proteins were obtained therefrom.

The thus-obtained intracellular proteins in an amount of 30 μg were loaded onto Novex 10% gelatin zymogram gel (Product No: EC61752, Invitrogen, USA), and electrophoresis was performed under the conditions of 4° C. and 100 V to isolate the proteins. Then, the gel was added into a renaturing buffer of 2.5% Triton X-100 and incubated at room temperature for 30 minutes, and then added into a developing buffer containing 0.2 M NaCl, 5 mM $CaCl_2$, 0.02% Brij35, and 50 mM Tris (pH 8.5), and left thereat at 37° C. for 24 hours. After being left thereat, the resultant was dyed with 0.5% Comassie Blue for 24 hours, and destained by placing in a destaining buffer containing 40% methanol and 10% acetic acid, and determined that the band clearly appearing in the zymogram gel represented a significant activity of gelatinase. An animal model not induced with spinal cord injury was used as the normal group, the negative control group was administered with physiological saline not containing fluoxetine and vitamin C, and the comparative control group was administered with fluoxetine or vitamin C alone after dissolving them in physiological saline at a concentration of 1 mg/kg or 100 mg/kg, respectively.

Figure 2A:
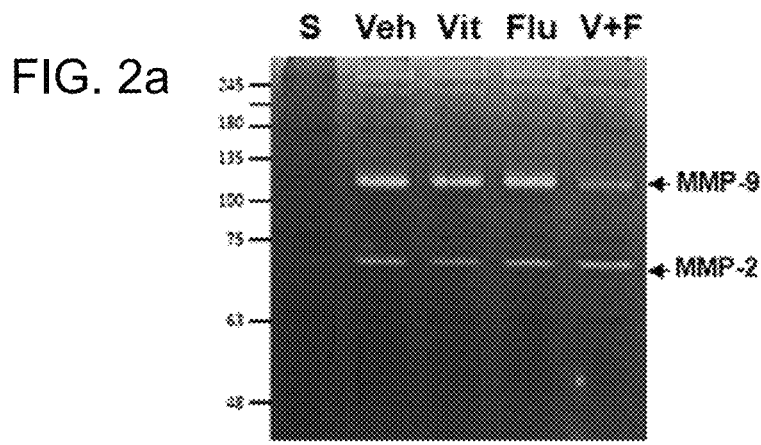
FIG. 2A shows the activities of MMP-9 and MMP-2 enzymes in an animal model with spinal cord injury.
Figure 2B:
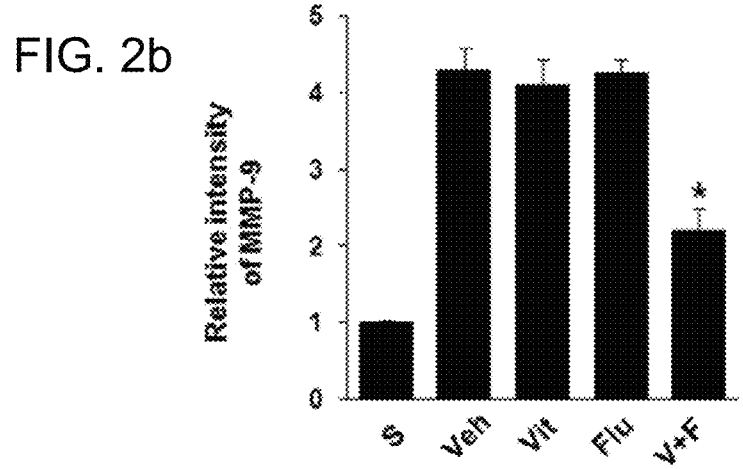
FIG. 2B shows the relative intensity of the activity of MMP-9 protein (* indicates the result of significant difference compared to that of negative control group (vehicle)).

As a result, as shown in FIG. 2, it was confirmed that the co-treatment of vitamin C and fluoxetine at a trace amount effectively decreased the activity of MMP-9 protein, whereas a single respective treatment at a trace amount showed a degree of activity of MMP-9 protein similar to that of the negative control group (FIGS. 2A and 2B).

EXAMPLE 4

Confirmation of the Effect of the Co-Treatment of Fluoxetine and Vitamin C Alleviating the Blood Infiltration after Spinal Cord Injury <4-1> Confirmation of Macrophage Marker Expression According to the Co-Treatment of Fluoxetine and Vitamin C after Spinal Cord Injury In order to confirm the effect of influx of inflammatory cells into blood vessels in an animal model after spinal cord injury, when they were co-treated, the degree of ED-1, which is a macrophage marker, was confirmed by Western blot.

Specifically, spinal cord tissue slices at a size of 10 μm were prepared in the same manner as in Example <1-2>, the spinal cord tissue slices were added with a lysis buffer containing octylphenoxy polyethoxy ethanol (Nonidet P-40, NP-40), 150 mM NaCl, 0.5% sodium deoxycholate, 0.1% SDS, and 50 mM Tris(pH 8.0), and intracellular proteins were obtained therefrom. The thus-obtained proteins were separated by SDS-PAGE and then transferred to a nitrocellulose membrane, reacted according to the manufacturer's protocol by treating with ED-1 (Serotec, USA), allowed to develop color with secondary antibody, thereby obtaining ED-1 protein. The expression of tubulin protein was confirmed by the control group for the comparison of expression, an animal model not induced with spinal cord injury was used as the normal group, the negative control group was administered with physiological saline not containing fluoxetine and vitamin C, and the comparative control group was administered with fluoxetine or vitamin C alone after dissolving them in physiological saline at a concentration of 1 mg/kg or 100 mg/kg, respectively.

As a result, as shown in FIG. 3, it was confirmed that the co-treatment of vitamin C and fluoxetine at a trace amount decreased the level of ED-1 expression to a level similar to that of the normal group, whereas a single respective treatment of vitamin C or fluoxetine at a trace amount showed a level of ED-1 expression similar to that of the negative control group (FIG. 3).

<4-2> Confirmation of the Effect of Influx of Blood Cells According to the Co-Treatment of Fluoxetine and Vitamin C after Spinal Cord Injury In order to confirm the effect of the co-treatment of fluoxetine and vitamin C on alleviating the influx of blood cells in an animal model after spinal cord injury, myeloperoxidase (MPO), which is a neutrophil marker, and ED-1, which is a macrophage marker, were confirmed by immunohistochemistry staining method.

Specifically, in an animal model with spinal cord injury prepared in Example <1-2>, spinal cord tissue slices at a size of 10 μm were prepared in the same manner as in Example <1-3>, 1 day and 5 days after the treatment with fluoxetine and vitamin C, myeloperoxidase (MPO; Dako, USA) and ED-1 (Serotec, USA) were reacted according to the manufacturer's protocol by respectively treating with primary antibody for immunohistochemistry staining, and then allowed to develop color with secondary antibody (Serotec, USA), thereby confirming MPO and ED-1. As the negative control group, the animal model with spinal cord injury was administered with physiological saline not containing fluoxetine and vitamin C.

As a result, as shown in FIG. 4, the animal model with spinal cord injury co-administered with fluoxetine and vitamin C showed a significant decrease in the expression of MPO and ED-1, compared to the negative control group (FIG. 4).

EXAMPLE 5

Preparation of an Animal Model with Transient Global Ischemia

<5-1> Preparation of an Animal Model with Transient Global Ischemia

Eight-week old adult male CD1 mice with a weight of 33 g to 37 g were induced to be anesthetized by injecting with 2% isoflurane under an air condition, in which nitrous oxide and oxygen were in a 70:30 ratio, and the mice were induced to have transient global ischemia according to the previous disclosure while the mice were maintained in the anesthetized state with 1% isoflurane (Kim, D. H. et. al, 2009. Food Chem. Toxicol. 47, 1473-1479.). The thus-prepared mice with transient global ischemia put into cages (4 mice/cage) were given ad libitum access to water and foods, and bred in an environment of a constant temperature (23±1° C.) and continuous humidity (60±10%) under a 12 hour light/dark cycle.

<5-2> Administration of Fluoxetine and Vitamin C

The experimental animals, after being induced to have transient global ischemia in Example <5-1>, were co-treated with fluoxetine and vitamin C, which were respectively dissolved in physiological saline at concentrations of 1 mg/kg and 100 mg/kg, once daily for 7 days. The negative control group was administered with physiological saline not containing fluoxetine and vitamin C, and the comparative control group was administered with fluoxetine or vitamin C alone after dissolving them in physiological saline at a concentration of 1 mg/kg or 100 mg/kg, respectively.

EXAMPLE 6

Confirmation of the Inhibitory Effect of the Co-Treatment of Fluoxetine and Vitamin C Against the Disruption of Brain Blood Barrier (BBB) after Transient Global Ischemia In order to confirm the effect of the co-treatment of fluoxetine and vitamin C on the disruption of blood-brain barrier after transient global ischemia, the change in permeability according to the disruption of the barrier in the fore brain of an animal model with transient global ischemia (whole model) was confirmed using Evans Blue dye.

Specifically, the animal model was induced to have transient global ischemia in the same manner as in Example <5-2> and, 7 days thereafter, was intraperitoneally administered with 5 mL of 2% Evans Blue dye dissolved in physiological saline, and the change in permeability of blood-brain barrier in the forebrain after transient global ischemia was confirmed by performing in the same manner as in <Example 2>.

An animal model not induced with transient global ischemia was used as the normal group, the negative control group was administered with physiological saline not containing fluoxetine and vitamin C, and the comparative control group was administered with fluoxetine or vitamin C alone after dissolving them in physiological saline at a concentration of 1 mg/kg or 100 mg/kg, respectively.

Figure 5A:
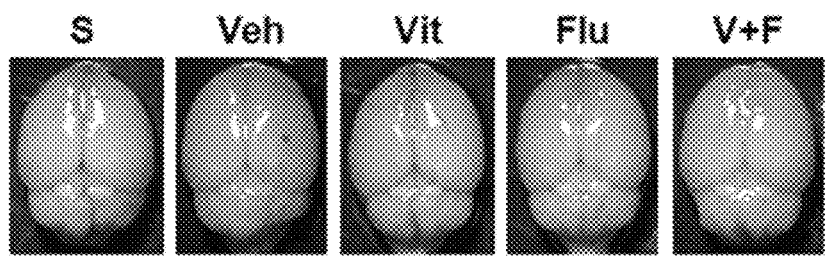
FIG. 5A shows the forebrains of animal models with transient global ischemia, in which Evans Blue dye was deposited.
Figure 5B:
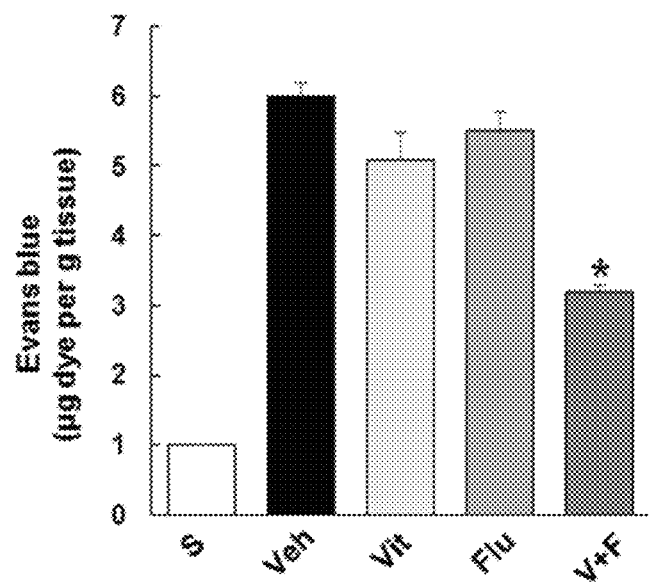
FIG. 5B shows the amount of Evans Blue dye quantitated in the forebrains of animal models with transient global ischemia (* indicates the result of significant difference compared to that of negative control group (vehicle)).

As a result, as shown in FIG. 5, it was confirmed that the co-treatment of vitamin C and fluoxetine at a trace amount significantly increased the inhibitory effect against the disruption of the blood-brain barrier, whereas a single respective treatment of vitamin C or fluoxetine at a trace amount showed a degree of permeability increase due to disruption of blood-brain barrier similar to that of the negative control group (FIGS. 5a and 5b).

EXAMPLE 7

Confirmation of the Effect of the Co-Treatment of Fluoxetine and Vitamin C on the Recovery of Memory Impairment after Transient Global Ischemia <7-1> Selection of an Animal Model with Transient Global Ischemia In order to confirm the effect of fluoxetine and vitamin C on memory recovery in mice induced with transient global ischemia, animal models with transient global ischemia were selected.

Specifically, mice were induced with transient global ischemia in the same manner as in Example <5-1>, and the cerebral blood flow of the mice induced with cerebral blood flow was measured using the Omegaflo FLO-N1 (Omegawave, Japan) and the mice which showed a decrease of less than 20% in cerebral blood flow compared to that of the normal mice were selected. The selected mice were administered with fluoxetine and vitamin C for 7 days by performing in the same manner as in Example <5-2> and thereby an animal model with transient global ischemia was prepared.

As a result, an animal model not induced with transient global ischemia was used as the normal group, the negative control group was administered with physiological saline not containing fluoxetine and vitamin C, and the comparative control group was administered with fluoxetine or vitamin C alone after dissolving them in physiological saline.

As a result, as shown in Table 1 below, a normal group, a negative control group, groups administered with vitamin C or fluoxetine alone, and a group co-administered with vitamin C and fluoxetine were selected (Table 1). Since the negative control group, the groups administered with vitamin C or fluoxetine alone, a group co-administered with vitamin C and fluoxetine selected above showed the amount of cerebral blood flow by less than 20% compared to that of the normal group, it was confirmed that there was no significant difference in the degree of ischemia among the groups.

TABLE 1

Cerebral blood flow of an animal model with transient global ischemia

| Normal Group | Negative Control Group | Group with Single Administration | | Co-administration of Vitamin C and Fluoxetine |
|---|---|---|---|---|
| | | Vitamin C | Fluoxetine | |
| 100 | 18.50 | 18.27 | 15.68 | 18.82 |
| 100 | 17.47 | 18.12 | 17.74 | 13.88 |
| 100 | 13.63 | 19.43 | 15.29 | 18.53 |
| 100 | 18.52 | 13.82 | 12.37 | 17.75 |

(* represents the rate of the cerebral blood flow reduced during occlusion when the cerebral blood flow was set at 100%.)

<7-2> Confirmation of the Effect of the Co-Treatment of Fluoxetine and Vitamin C on the Recovery of Memory Impairment Regarding Hippocampal-Dependent Short-Term Memory after Transient Global Ischemia In order to confirm the effect of the co-treatment of fluoxetine and vitamin C on the recovery effect regarding the hippocampal-dependent short-term memory occurring after transient global ischemia, Y-maze test was performed.

Specifically, a three-arm horizontal maze, which consists of black opaque polyvinyl plastic with a wall height of 12 cm, a length of 40 cm, and a width of 3 cm connected with an angle of 120°, was prepared according to the previous disclosure (Kim, D. H. et. al, 2009. Food Chem. *Toxicol.* 47, 1473-1479.). Then, the selected mice were located in one of the arms of the prepared maze, and the sequence and the number that the mice entered each arm for 8 minutes (e.g., ABCCAB) were recorded. The number selected by continuously connecting all three arms (e.g., ABC, CAB, or BCA) was defined by spontaneous alternation, and the percentage of alternation was calculated by the equation 1 below. For removing the odors remaining after the experiment, the maze was washed with water.

$$\text{alternation rate}(\%) = (\text{total number of alternations}/\text{the number entered the total arms} - 2) \times 100 \quad [\text{Equation 1}]$$

The number that the mice entered the total arms represents the locomotor activity.

Figure 6A:
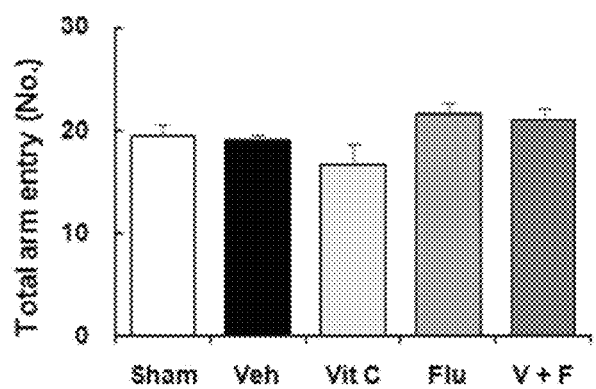
FIG. 6A shows the percentage of spontaneous alternation of an animal model with transient global ischemia in a Y-maze experiment.
Figure 6B:
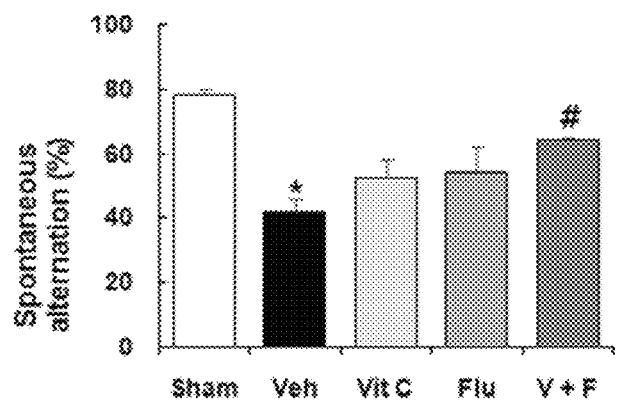
FIG. 6B shows the number of total arm entries by an animal model with transient global ischemia into the total arms (* indicates the result of significant difference compared to that of normal group (sham) and # indicates the result of significant difference compared to that of negative control group (vehicle)).

As a result, as shown in FIG. 6, there was no significant difference in the locomotor activity among all experimental groups (FIG. 6A), but the negative control group showed a decrease in memory, and in contrast, the group co-treated with fluoxetine and vitamin C showed a significant effect of memory recovery (FIG. 6B).

<7-3> Confirmation of the Effect of the Co-Treatment of Fluoxetine and Vitamin C on the Recovery of Hippocampal Cell Injury after Transient Global Ischemia In order to confirm the effect of the co-treatment of fluoxetine and vitamin C on the recovery of hippocampal injury occurring after transient global ischemia, the CA1 neuron region of hippocampal tissue was stained.

Specifically, the brains obtained and stored by performing in the same manner as in <Example 6> were cut into 30 μm coronal plane sections, placed on gelatin-coated slides, stained with crystal violet, and dehydrated by adding 70%, 80%, 90%, and 100% alcohol in this order. Upon dehydration, xylene was added thereto, covered with coverslips, and the CA1 neuron region of hippocampal tissue was observed. An animal model not induced with spinal cord injury was used as the normal group, the negative control group was administered with physiological saline not containing fluoxetine and vitamin C, and the comparative control group was administered with fluoxetine or vitamin C alone after dissolving them in physiological saline.

As a result, as shown in FIGS. 7 and 8, it was confirmed that the co-treatment of vitamin C and fluoxetine at a trace amount significantly recovered the hippocampal tissue injury to a level similar to that of the normal group, whereas a single respective treatment of vitamin C or fluoxetine at a trace amount showed a recovery similar to that of the negative control group (FIGS. 7 and 8).

PREPARATION EXAMPLE 1

Preparation of Pharmaceutical Powders

<1-1> Preparation of Powders

| | |
|---|---|
| fluoxetine and vitamin C of the present invention | 0.1 g |
| lactose | 1.5 g |
| talc | 0.5 g |

The above ingredients were mixed and filled into a sealed pouch to prepare powders.

<1-2> Preparation of Tablets

| | |
|---|---|
| fluoxetine and vitamin C of the present invention | 0.1 g |
| lactose | 7.9 g |
| crystalline cellulose | 1.5 g |
| magnesium stearate | 0.5 g |

The above ingredients were mixed and prepared into tablets by direct tableting method.

<1-3> Preparation of Capsules

| | |
|---|---|
| fluoxetine and vitamin C of the present invention | 0.1 g |
| corn starch | 5 g |
| carboxy cellulose | 4.9 g |

The above ingredients were mixed to prepare powders, and the powers were filled into hard capsules according to the conventional capsule preparation method to prepare capsules.

<1-4> Preparation of Injections

| | |
|---|---|
| fluoxetine and vitamin C of the present invention | 0.1 g |
| sterile distilled water for injection | adequate |
| pH adjuster | adequate |

Injections were prepared to contain the ingredients in the amount described above in 2 mL ampoules according to the conventional method of preparing injections.

<1-5> Preparation of Liquids

| | |
|---|---|
| fluoxetine and vitamin C of the present invention | 0.1 g |
| isomerized sugar | 10 g |
| mannitol | 5 g |
| distilled water | adequate |

According to the conventional method for liquid preparation, each ingredient was dissolved in distilled water, added with an adequate amount of a lemon flavor, the ingredients described above were mixed. Then, distilled water was added thereto to a final volume of 100, filled into a brown bottle, and sterilized to prepare liquids.

PREPARATION EXAMPLE 2

Preparation of Health Foods

<2-1> Preparation of Wheat Flour Foods

Fluoxetine and vitamin C of the present invention in an amount of from 0.5 part by weight to 5.0 parts by weight, respectively, were added to wheat flour, and the resulting mixture was used to prepare bread, cakes, cookies, crackers, and noodles.

<2-2> Preparation of Soups and Gravies

Fluoxetine and vitamin C of the present invention in an amount of from 0.1 part by weight to 5.0 parts by weight, respectively, were added to soups and gravies to prepare meat-processed products, noodle-style soups and gravies for health improvement.

<2-3> Preparation of Ground Beef

Fluoxetine and vitamin C of the present invention in an amount of 10 parts by weight, respectively, were added to ground beef to prepare ground beef for health improvement.

<2-4> Preparation of Dairy Products

Fluoxetine and vitamin C of the present invention in an amount of from 5 parts by weight to 10 parts by weight, respectively, were added to milk to prepare dairy products such as butter and ice cream.

<2-5> Preparation of Dry Cereal

Unpolished rice, barley, and glutinous rice were pregelatinized by a conventional method, dried, roasted, and prepared into powders by a pulverizer to have a particle size of 50 mesh.

Black beans, black sesame, and perilla seeds were also steamed and dried by a conventional method, roasted, and prepared into powders by a pulverizer to have a particle size of 50 mesh.

Fluoxetine and vitamin C of the present invention were concentrated under reduced pressure, sprayed, and dried by hot air dryer, and the resulting dry product was prepared into powders by a pulverizer to have a particle size of 50 mesh.

The thus-prepared grains, seeds and nuts, and fluoxetine and vitamin C of the present invention are prepared by the mixing ratio described below.

Grains (unpolished rice (30 parts by weight), adlay (15 parts by weight), and barley (20 parts by weight))

Seeds and nuts (perilla seeds (7 parts by weight), black beans (8 parts by weight), black sesame (7 parts by weight)).

An extract of *Saururus chinensis* of the present invention, a fraction thereof, a compound of the following Formula 1 isolated therefrom, or a pharmaceutically acceptable salt thereof (3 parts by weight)

*Ganoderma lucidum* (0.5 part by weight)

*Rehmannia glutinosa* (0.5 part by weight)

<2-6> Preparation of Health Supplementary Foods

| | |
|---|---|
| fluoxetine and vitamin C of the present invention | 100 mg |
| vitamin mixture | adequate |
| vitamin A acetate | 70 µg |
| vitamin E | 1.0 mg |
| vitamin B1 | 0.13 mg |
| vitamin B2 | 0.15 mg |
| vitamin B6 | 0.5 mg |
| vitamin B12 | 0.2 µg |
| vitamin C | 10 mg |
| biotin | 10 µg |

-continued

| | |
|---|---|
| nicotinic acid amide | 1.7 mg |
| folic acid | 50 µg |
| calcium pantothenate | 0.5 mg |
| inorganics mixture | adequate |
| ferrous sulfate | 1.75 mg |
| zinc oxide | 0.82 mg |
| magnesium carbonate | 25.3 mg |
| potassium phosphate | 15 mg |
| dicalcium phosphate | 55 mg |
| potassium citrate | 90 mg |
| calcium carbonate | 100 mg |
| magnesium chloride | 24.8 mg |

The composition ratio of the mixture of vitamin and mineral is a preferred embodiment prepared based on relatively appropriate ingredients for health foods. However, the mixing ratio may be practiced after a random modification, and the above ingredients may be mixed according to a conventional method of preparing health foods to prepare granules, which may be used for the preparation of a health food composition according to a conventional method.

PREPARATION EXAMPLE 3

Preparation of Health Drinks

| | |
|---|---|
| fluoxetine and vitamin C of the present invention | 100 mg |
| citric acid | 100 mg |
| oligosaccharide | 100 mg |
| plum concentrate | 2 mg |
| taurine | 100 mg |
| distilled water | to a final volume of 500 mL |

The above ingredients are mixed according to the method of a conventional method of preparing health drinks, heat stirred at 85° C. for about 1 hour, and the resulting solution was filtered and received in a 1 L container, sealed and sterilized, and frozen-stored to be used for the preparation of a composition for health drinks of the present invention.

The composition ratio is a preferred embodiment prepared based on relatively favored ingredients for health drinks. However, the mixing ratio may be practiced after a random modification, and the above ingredients may be mixed according to the regional and national preferences such as the consumer class, the countries in need of the same, the purposed uses, etc.

INDUSTRIAL APPLICABILITY

As described above, the co-administration with fluoxetine and vitamin C of the present invention shows a significant effect in a low concentration, in which the single administration of fluoxetine or vitamin C does not show any effect of alleviation regarding the disruption of the blood-brain barrier and the blood-spinal cord barrier, and the result suggests a synergy effect and reduced side effect due to the administration of the compounds in a low concentration. Therefore, fluoxetine and vitamin C of the present invention can be effectively used for a pharmaceutical composition for the prevention and treatment of blood-brain barrier disorder and central nervous system diseases.

The invention claimed is:

1. A method for treating a spinal cord injury, comprising administering fluoxetine and vitamin C to a subject having the spinal cord injury, wherein the fluoxetine and vitamin C are administered in a ratio of from 1:500 to 1:10; wherein the fluoxetine is administered in an amount of from 0.8 mg/kg to 2 mg/kg to the subject; and wherein the vitamin C is administered in an amount of from 70 mg/kg to 150 mg/kg to the subject.

2. The method of claim 1, wherein the fluoxetine and vitamin C are co-administered to the subject.

3. The method of claim 2, wherein the fluoxetine and vitamin C are co-administered to the subject in a composition comprising the fluoxetine and vitamin C.

4. The method of claim 1, wherein the method consists essentially of administering fluoxetine and vitamin C to the subject.

* * * * *